US010653737B1

(12) United States Patent
Dhamane et al.

(10) Patent No.: US 10,653,737 B1
(45) Date of Patent: May 19, 2020

(54) SYNERGISTIC NUTRITIONAL COMPOSITIONS FOR PAIN MANAGEMENT

(71) Applicant: Celagenex Research (India) Pvt. Ltd., Thane (IN)

(72) Inventors: Dhiraj Dhamane, Kalyan-Thane (IN); Rajendra Prasad Tongra, Jaipur (IN)

(73) Assignee: Celagenex Research (India) PVT. LTD., Thane, Maharashtra (IN)

( * ) Notice: Subject to any disclaimer, the term of this patent is extended or adjusted under 35 U.S.C. 154(b) by 0 days.

(21) Appl. No.: 16/733,100

(22) Filed: Jan. 2, 2020

(30) Foreign Application Priority Data

Jan. 2, 2019 (IN) .............................. 201921000092

(51) Int. Cl.
*A61K 36/21* (2006.01)
*A61P 25/02* (2006.01)
*A61K 9/00* (2006.01)
*A61K 31/164* (2006.01)

(52) U.S. Cl.
CPC ............ *A61K 36/21* (2013.01); *A61K 9/0053* (2013.01); *A61K 31/164* (2013.01); *A61P 25/02* (2018.01)

(58) Field of Classification Search
CPC .... A61K 36/21; A61K 9/0053; A61K 31/164; A61P 25/02
See application file for complete search history.

(56) References Cited

U.S. PATENT DOCUMENTS 9,561,249 B2 2/2017 Kevil et al.
9,649,334 B2 5/2017 Kevil et al.
9,801,836 B2 10/2017 Della Valle et al.
9,833,426 B2 12/2017 Morita et al.
10,383,903 B2 8/2019 Antony
10,441,559 B2 * 10/2019 Della Valle ........ A61K 31/7034
(Continued)

FOREIGN PATENT DOCUMENTS

JP 2012041296 A 3/2012
JP 2013227256 A 11/2013
(Continued)

OTHER PUBLICATIONS

"Pain (Chronic and Acute)" MedicineNet, Willian C. Shiel,Jr., Medical Author, pp. 1-3 (2017) https://www.medicinenet.com/pain_acute_and_chronic/views.htm.
(Continued)

*Primary Examiner* — Aaron J Kosar
(74) *Attorney, Agent, or Firm* — Melissa M. Hayworth; E. Joseph Gess

(57) ABSTRACT

The present invention discloses a synergistic nutritional composition(s) for pain management. Particularly, the invention relates to synergistic nutritional composition comprising specific combination of palmitoylethanolamide (PEA) and standardized red spinach extract enriched with nitrate content, present in the ratio of 1:0.1 to 1:5 along with pharmaceutically acceptable carriers/excipients. More particularly the invention discloses synergistic nutritional composition comprising combination of PEA and nitrate of the red spinach extract, which are present in the ratio of 1:0.01 to 1:0.5. Further the instant synergistic composition is useful for treating neuropathic pain, particularly in the treatment of subject suffering with diabetic peripheral neuropathy and/or small fiber neuropathy.

18 Claims, 4 Drawing Sheets

(56) References Cited

U.S. PATENT DOCUMENTS

2017/0252314 A1* 9/2017 Della Valle .......... A61K 9/1647
2019/0070133 A1* 3/2019 Singh .................... A61K 45/06

FOREIGN PATENT DOCUMENTS

| WO | 2013063263 A1 | 5/2013 |
| WO | 2016146453 A1 | 9/2016 |
| WO | 2016183134 A1 | 11/2016 |

OTHER PUBLICATIONS

Pop-Busui, R., et al., "Diabetic Neuropathy: A Position Statement by the American Diabetes Association" American Diabetes Association, Diabetes Care 40:136-154 (2017).

Langley, P.C., et al., "The burden associated with neuropathic pain in Western Europe", Journal of Medical Economics 16(1):85-95 (2013).

Saxena A.K., et al., "Pharmacological management of neuropathic pain in India: A consensus statement from Indian experts", Indian J Pain 32(3)132-144 (2018). http://www.indianjpain.org on Monday, Mar. 9, 2020.

Schifilliti, C., et al., Micronized Palmitoylethanolamide Reduces the Symptoms of Neuropathic Pain in Diabetic Patients, Pain Res Treat V 2014 ID 849623: 1-5 (2014).

Jin Bo Su, "Vascular endothelial dysfunction and pharmacological treatment", World J Cardiol. 7(11): 719-741 (2015).

Zhou, S., et al., "Repression of P66Shc Expression by SIRT1 Contributes to the Prevention of Hyperglycemia-Induced Endothelial Dysfunction", Circ Res. 109(6):639-648 (2011).

Chlopicki, S., et al., "1-Methylnicotinamide (MNA), a primary metabolite of nicotinamide, exerts anti-thrombotic activity mediated by a cyclooxygenase-2/prostacyclin pathway", Br J Pharmacol. 152(2): 230-239 (2007).

Turck, D., et al., "Safety of 1-methylnicotinamide chloride (1-MNA) as a novel food pursuant to Regulation (EC) No. 258/97", EFSA Journal, 15(10):5001; p. 1-16 (2017). www.efsa.europa.eu/efsajournal.

Lundberg, J. O., and Mirco Govoni, "Inorganic Nitrate Is a Possible Source for Systemic Generation of Nitric Oxide", Free Radical Biol Med. vol. 37(3); p. 395-400 (2004).

Champion, H.C., et al., "Phosphodiesterase-5A dysregulation in penile erectile tissue is a mechanism of priapism", PNAS 102(5):1661-1666 (2005). www.pnas.org/cyi/doi/10.1073/pnas.0407183102.

Cines, D. B., et al. "Endothelial Cells in Physiology and in the Pathophysiology of Vascular Disorders", Blood-The Journal of the American Society of Hematology, 91(10), pp. 3527-3561 (1998).

Griscavage, J.M., et al., "Negative Modulation of Nitric Oxide Synthase by Nitric Oxide and Nitroso Compounds", Adv. Pharmacol v. 34, pp. 215-234 (1995).

* cited by examiner

SYNERGISTIC NUTRITIONAL COMPOSITIONS FOR PAIN MANAGEMENT

TECHNICAL FIELD

The invention relates to synergistic nutritional compositions for pain management. Particularly, the invention relates to synergistic nutritional composition for treating pain and pain related disorders, comprising specific combination of fatty acid amide compound and nitric oxide donor, wherein the fatty acid amide compound is palmitoylethanolamide and nitric oxide donor is naturally extracted inorganic nitrate/nitrite.

Further the instant synergistic composition is useful for treating neuropathic pain, particularly in the treatment of subject suffering with diabetic peripheral neuropathy and small fiber neuropathy.

BACKGROUND AND PRIOR ART

Pain is an unpleasant sensation in animals that is caused by actual or perceived injury to body tissues and produces physical and emotional reactions. Presumably, pain sensation has evolved to protect our bodies from harm by causing us to perform certain actions and avoid others. Pain might be called as a protector, a predictor, or simply a hassle (William C. Shiel, 'Pain Management' Medicine Net, June 2018).

We all experience pain to greater or lesser extent at various points of our lives. Plausibly pain is the most common reason that patients seek medical attention. But, each of us perceives a given pain stimulus in our own unique manner. The intensity of the response to a pain stimulus is largely subjective.

Pain is actually a wide spectrum of disorders including acute pain, chronic pain and cancer pain and sometimes a combination of these. Pain can also arise for many different reasons such as surgery, injury, nerve damage, physical changes; changes in mood; decrease in appetite; and metabolic problems such as diabetes.

'Nerve pain' is often caused due to nerve damage. Nerve damage from diabetes is called diabetic neuropathy. About half of all people with diabetes have some form of nerve damage. It is more common in those who have had the disease for a number of years and can lead to many kinds of health problems.

The damaged nerve performs functions abnormally. It may become quiet and send no information, which causes numbness, or it may send excessive and inappropriate pain messages.

Typically pain is classified as either acute or chronic. Acute pain is of abrupt onset and is usually the result of a clearly defined cause such as an injury. Acute pain resolves with the healing of its underlying cause.

On the other side chronic pain persists for weeks or months and is usually associated with an underlying condition, such as arthritis. The severity of chronic pain can be mild, moderate, or severe. The chronic pain is associated with lower back pain, arthritis, headache, multiple sclerosis, fibromyalgia, shingles, nerve damage, or cancer. In some instances the pain is neuropathic pain, inflammatory pain, nociceptive pain, functional pain, musculo-skeletal pain, peripheral and central nervous system pain.

'Neuropathic pain' is pain caused by damage or disease that affects the nervous system.

Classic examples of this pain are shingles and diabetic peripheral neuropathy. Diabetic peripheral neuropathy (DPN) damages two different types of nerves close to the surface of human skin. DPN can affect small nerves that protect human body by sending signals about pain and temperature changes to brain. This condition can also attack large nerves that detect touch, pressure and help to keep a balance. Most people with DPN have damage to both types of nerves [American Diabetes Association. Diabetes Care 2017; 40:136-154.]

DPN usually affects extremities like feet, hands, legs and arms, where nerve fibers are the longest and most numerous. The International Association for the Study of Pain (IASP) defines 'neuropathic pain' as pain caused by a lesion or disease of the somatosensory nervous system, which causes unpleasant and abnormal sensation (dysesthesia), an increased response to painful stimuli (hyperalgesia), and pain in response to a stimulus that does not normally provoke pain (allodynia).

According to recent studies, it is observed that neuropathic pain affects about 1 in every 10 adults and the economic burden for treating this pain is increasing. Langley et al [J Med Econ. 2013; 16(1):85-95] have described economical and social impact of neuropathic pain (NeP) on health-related quality-of-life in Western Europe.

Neuropathic pain [NeP] severity is associated with loss of productivity and needs more visits to the physician and higher number of medications for treatment. The economic burden of NeP is a significant concern in developing countries like India. Neuropathic pain [NeP] is a severe and debilitating condition which affects approximately 4 million people in the India alone. Though reports are limited on the prevalence of NeP, the burden of NeP in India is enormous. In a recent evaluation from India, the reported prevalence of diabetic peripheral neuropathy (DPN) was 29.2% in patients with type 2 diabetes mellitus (T2DM). A recent consensus document from India provides recommendations for pharmacological treatment of pain. However, despite the knowledge of damaging complications of neuropathies, there are no specific guidelines or consensus recommendations on the diagnosis and treatment of NeP in Indian setting [Indian Journal of Pain, 32,3, 2018].

Particularly, neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain.

There are further types of neuropathy such as autonomic neuropathy which affects the autonomic nerves, which control the bladder, intestinal tract, and genitals, among other organs; neuropathic arthropathy; cranial neuropathy, compression mononeuropathy, femoral neuropathy, diabetic amyotrophy, focal neuropathy, thoracic or lumbar radiculopath.

The treatment of pain is guided by the history of the pain, its intensity, duration, aggravating and relieving conditions, and structures involved in causing the pain. In order for a structure to cause pain, it must have a nerve supply, be susceptible to injury, and stimulation of the structure should cause pain. The concept behind most interventional procedures for treating pain is that there is a specific structure in the body with nerves of sensation i.e. generating the pain.

Pain management has crucial role in identifying the precise source of the problem and isolating the optimal treatment.

There are mainly four types of pharmacological therapies for neuropathic pain that are widely used in the medical sector: antidepressants, anticonvulsants, opioids, and topical agents.

The first-line treatments for neuropathic pain, based on efficacy and safety, include antidepressants (e.g., tricyclic antidepressants [TCAs], serotonin-norepinephrine reuptake inhibitors [SNRIs]) and certain anticonvulsants (e.g., gabapentin, pregabalin, and topical lidocaine). Opioid analgesics have been recommended as second-line treatments, given their safety; however, they are sometimes used as first choice. Third-line treatments include certain antidepressant medications (e.g., bupropion, citalopram, and paroxetine) and certain anticonvulsants medications (e.g., carbamazepine, lamotrigine, oxcarbazepine, and N-methyl-D-aspartate [NMDA] receptor antagonists). However, these drugs are not completely effective in attenuating neuropathic pain, because of the complexity of this type of pain, and also accompanied with side effects, such as sedation, dizziness, edema, and ataxia. For these reasons, there is interest developed in finding alternate non toxic, environmentally friendly agents for relieving neuropathic pain.

Diet and nutrition are frequently overlooked as a first-line tool for pain relief. It is observed that certain nutrients can influence pain without causing side effects; such nutrients also may present as therapeutic candidates for the development of new drugs to alleviate neuropathic pain.

Further the neuroinflammation, which is characterized by infiltration of immune cells, activation of mast cells and glial cells, and production of inflammatory mediators in the peripheral and central nervous systems, plays an important role in the induction and maintenance of chronic pain and neuropathic pain.

In the past few years fatty acid amides are found to be effective to relieve the chronic inflammatory and neuropathic pain. Fatty acid amides include anandamide (N-arachidonoylethanolamine), oleamide, palmitoylethanolamide (PEA), and oleoylethanolamide (OEA).

Among fatty acid amides PEA, an endogenous fatty acid amide belonging to the N-acylethanolamines family, exhibit efficacious results in patients with chronic pain associated to a variety of pathological conditions.

'PEA' is effective and safe in the management of chronic pain in different pathological conditions, without any adverse effects.

Schifilliti C, et al. discloses therapeutic use of micronized palmitoylethanolamide for reducing symptoms of neuropathic pain in diabetic patients. (*Pain Res Treat* 2014; 2014: 849623).

US20170252314A1 discloses method for controlling the inflammatory and/or neuropathic pain of various origins by administering a pharmaceutical composition comprising palmitoylethanoiamide (PEA) and L-acetylcarnitine (LAC), optionally in addition with an antioxidant compound, such as a polyphenol, alpha-lipoic acid, or 1-acetylcysteine to a patient.

U.S. Pat. No. 9,801,836B2 discloses pharmaceutical compositions comprising N-palmitoylethanolamide as an analgesic in combination with opioids for treating pain conditions.

It is reported that 'opioids' are effective to some extent in reducing the intensity of some neuropathic pain states. However, these drugs commonly cause side effects expressed as cognitive ability, constipation and nausea, and their use is further limited by the risk of abuse of the opioid.

WO2016183134A1 discloses composition comprising palmitoylethanolamide and salicylate for reducing or alleviating pain in a subject in need thereof.

WO2016146453A1 relates to composition comprising palmitoylethanolamide (PEA) and a vitamin B for alleviating neuropathic pain and method for preparing such a composition.

WO2013063263A1 discloses compositions comprising anti-depressant agomelatine or related compounds together with palmitoylethanolamide (PEA) as a co-factor, for the prevention or treatment of neuropathic pain.

Currently, various drugs are used to combat neuropathic pain, though without reaching the desired level of success for the patient. Side effects induced by current prescribed pain-relieving drugs limit their use by making it impossible to reach effective dose levels. So, there is a need for effective and safe treatment options for patients suffering from neuropathic pain.

Accordingly, research continues into new or alternative remedy for treating neuropathic pain in a manner that is long lasting, effective, with few side effects and good tolerability.

The disabling human syndrome of "neuropathic pain" is difficult complication of peripheral or central nerve injury or degeneration. A complex interaction between injured peripheral axons, sensory neurons and central nervous system signaling is intended to account for it.

It is evident that that the free radical signaling molecule, nitric oxide (NO) may act at several levels of the nervous system during the development of experimental neuropathic pain. It may be an important player in the cascade of events that generate neuropathic pain.

'Nitric Oxide' (NO) may be involved in the mechanisms of pain generation and transmission throughout the central and peripheral nervous systems (including brain and spinal cord and perivascular tissue and peripheral nerve terminals) and locally released pain mediators (including formation of inflammation and vascular edema). These novel observations prescribe new approaches to the pharmacologic treatment of neuropathic pain, and other forms of chronic, intractable pain that are resistant to classical pharmacotherapy.

U.S. Pat. No. 9,649,334B2 pertains to a method of treating peripheral neuropathy in a human subject, the method comprising: orally administering to the subject a pharmaceutical composition comprising about 40 mg of sodium nitrite one or two times per day for at least ten days.

U.S. Pat. No. 9,561,249B2 discloses a method of treating or reducing neuropathic pain, said method consisting of orally administering to a subject in need thereof a tablet or capsule formulated for sustained release of inorganic nitrite i.e. KNO2 or NaNO2.

U.S. Ser. No. 10/383,903B2 discloses an extract of amaranth, having enriched nitrate content, L-arginine, flavonoids, saponins, alkaloids, carbohydrates, proteins, potassium, for lowering the blood pressure (hypertension) and increasing the endurance.

The new strategies of pharmacologic pain treatment are increasing rapidly due to the availability of new drugs modulating the NO-activated cascade.

To overcome the side effect of opioids and other analgesic substances in pharmacologic pain treatment, the present inventors have successfully formulated synergistic nutritional composition of fatty acid amide in presence of NO modulator.

OBJECTIVE OF THE INVENTION

The primary object of the present invention is to provide synergistic nutritional composition for pain management.

Another object of the present invention is to provide synergistic composition comprising active nutrients that significantly reduce neuropathic pain without any adverse effects.

Yet another object of the present invention is to cater nutritional composition that gives synergistic effect for alleviating nerve pain by controlling nerve sensation and restoring normal function of affected nerves through vasodilation.

SUMMARY OF THE INVENTION

To meet the above objectives, the inventors of the instant invention have carried out thorough experiments to establish synergistic combination of instant bioactive ingredients or nutritional supplements or dietary supplements or micronutrients or natural substances or metabolic intermediates or bioenergetic agents or biochemicals or organic molecules that ameliorate neuropathic pain in a subject in need thereof.

In an aspect, the invention relates to synergistic nutritional composition of active ingredients for pain management.

In another aspect, the invention relates to synergistic nutritional composition comprising of fatty acid amide and nitric oxide donor for regulating/managing pain and/or pain related disorders.

In yet another aspect, the invention provides potent synergistic nutritional composition comprising combination of fatty acid amide and nitric oxide donor in an effective ratio, wherein the said fatty acid amide is palmitoyletanolamide and nitric oxide donor is inorganic nitrate/nitrite derived from natural extract.

In another aspect, the instant invention provides synergistic nutritional compositions comprising combination of palmitoyletanolamide and inorganic nitrate/nitrite for treating the subject suffering from chronic pain, preferably neuropathic pain.

In yet another aspect, the invention relates to synergistic compositions comprising combination of palmitoyletanolamide, which is present in the range of 1 to 500 mg and inorganic nitrate/nitrite present in the range of 1 to 100 mg, along with pharmaceutically acceptable excipients/carriers.

In yet another aspect, the invention relates to synergistic nutritional composition, which is useful for treating diabetic neuropathy. Moreover, the one active moiety-palmitoyletanolamide controls mast cell activity and other moiety-nitrate improves nitric oxide mediated vasodilation that subsequently ameliorates delivery of oxygen and nutrients to affected nerves.

In yet another aspect, the invention provides non-toxic, cost-effective, nutrient based composition for improving neuropathic pain.

Abbreviations
NO: Nitric Oxide
$NO_3^-$: Nitrate
$NO_2^-$: Nitrite
PEA: Palmitoyletanolamide
NeP: Neuropathic Pain
IN: Inorganic Nitrate
NGF: Nerve growth factor
DPN: Diabetic peripheral neuropathy
RT-PCR: Reverse transcription-polymerase chain reaction
GAPDH: Glyceraldehyde 3-phosphate dehydrogenase
TAE: Tris-acetate-EDTA buffer
EDTA: Ethylenediaminetetraacetic acid
eNOS: endothelial nitric oxide synthase

DETAILED DESCRIPTION

Figure 1:
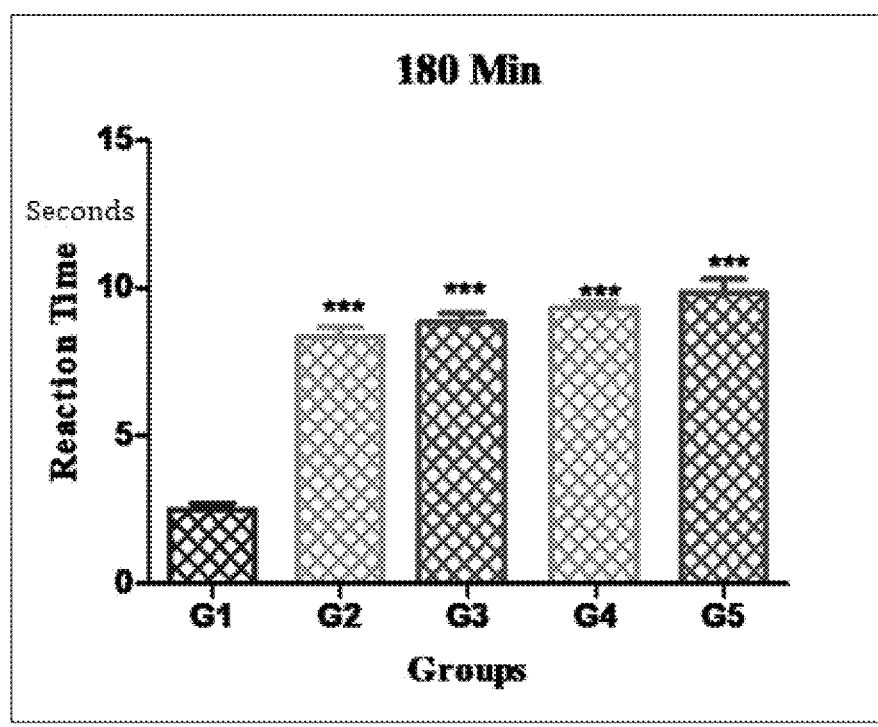
FIG. 1 depicts modulatory effect of test substances on Tail Immersion Latency reaction time at 180 Min.
Figure 2:
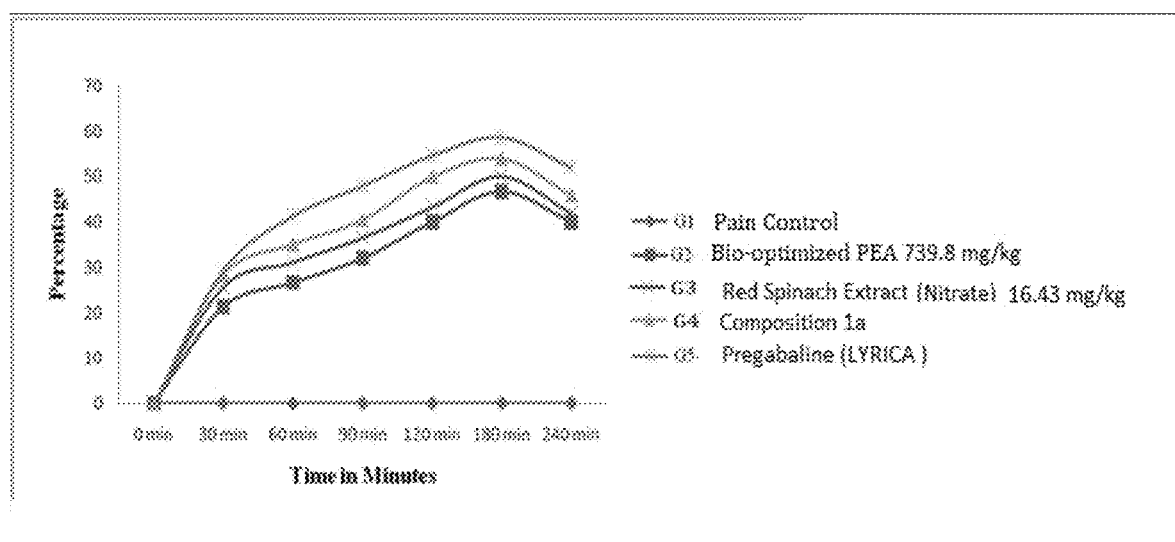
FIG. 2 depicts effect of test substances on percentage maximum possible effect G1—Pain Control; G2—Bio-optimized PEA [739.8 mg/kg]; G3—Red Spinach Extract (Amaranthus cruentus) (enriched with Inorganic nitrate) [16.43 mg/kg]; G4—Composition 1a; G5—Pregabalin (LYRICA® 75 mg).
Figure 3:
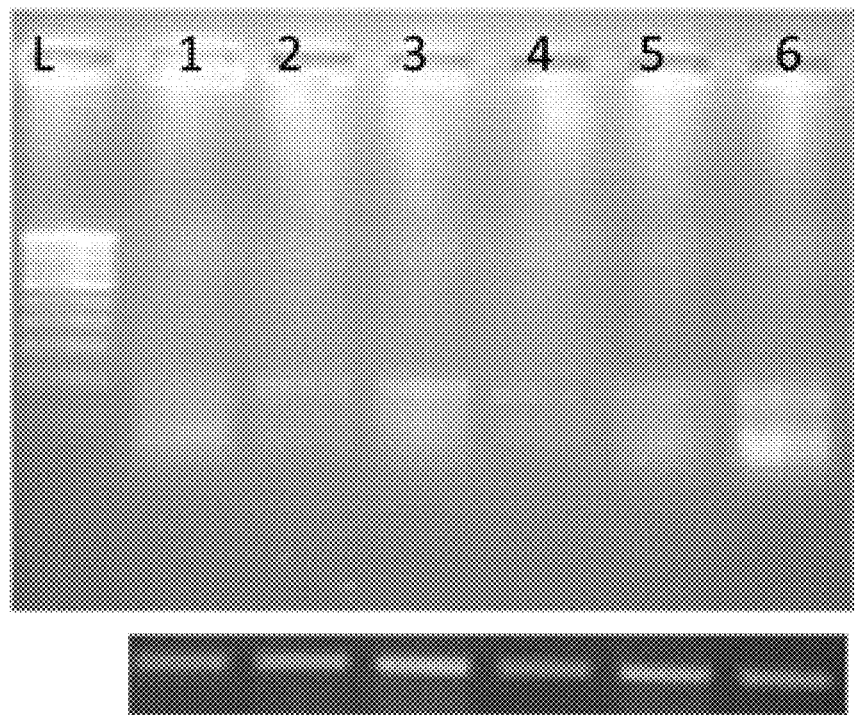
FIG. 3 depicts semi-quantitative RT-PCR profile of eNOS gene amplified in H9C2 with G2, G3 and G4 [L—100 bp ladder, 1—cell control, 2—Pregabalin (125 µg/ml), 3—G2 (500 µg/ml), 4—G3 (500 µg/ml), 5—G4 (Composition 1a), 6—TNF-alpha induced cells).
Figure 4:
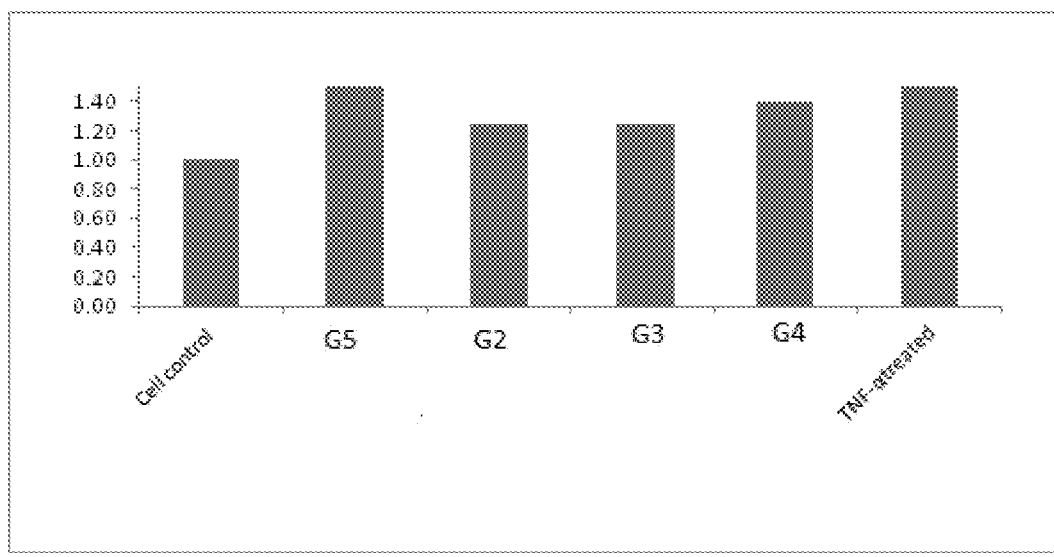
FIG. 4 depicts Semi quantitative densitometric analysis of gene transcripts from G2, G3, G4 treated cells; the relative level of eNOS gene expression is normalized to β-Actin.

The invention will now be described in detail in connection with certain preferred and optional embodiments, so that various aspects thereof may be more fully interpreted and comprehended. However, any skilled person or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the state of art.

The singular forms "a," "an," and "the" include plural reference unless the context clearly dictates otherwise.

The term 'nutritional composition' does not limit the scope of the invention only for nutrients but it also includes food supplements, dietary supplements, plant extracts, herbal products which are resourced from natural products that eventually contribute to therapeutic effect in a subject.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Particularly the term "pharmaceutically-acceptable salts" refers to the relatively non-toxic, inorganic and organic acid addition salts of compounds, as well as solvates, co-crystals, polymorphs and the like of the salts.

In a preferred embodiment, the invention relates to synergistic nutritional composition comprising combination of PEA and inorganic nitrate/nitrite or nutraceutically acceptable salts thereof, for treating neuropathic pain in a subject in need thereof.

In another embodiment, the invention discloses synergistic composition, wherein the fatty acid amide moiety is palmitoyletanolamide (PEA), for controlling mast cell activity and thereby relieving pain sensation.

Palmitoylethanolamide (PEA), an endogenous fatty acid amide, is a congener of the endocannabinoid anandamide (AEA) that belongs to a class of lipid mediators, the superfamily of N-acylethanolamines. PEA is a natural compound, and found in a variety of food products, such as soybean lecithin, egg yolk, and peanut meal.

Palmitoylethanolamide (PEA) can also be referred as 'Hydroxyethylpalmitamide', 'Palmidrol', 'N-Palmitoylethanolamine', 'Palmitylethanolamide'.

Due to lipophilic nature and large particle size in the native state, molecules of PEA have limitations in terms of solubility and bioavailability. The micronization technique is frequently used in the pharmaceutical field to enhance the dissolution rate of drug and thereby reduce variability of drug absorption when orally administered.

In another embodiment, the palmitoylethanolamide (PEA) can be used in various forms including but not limited to non-micronized form (nm-PEA), micronized form (m-PEA), or ultra-micronized form (um-PEA).

In some embodiments the composition comprising micronized palmitoylethanolamide (m-PEA) having particle size in the range of 2 μm-10 μm.

In another embodiment, the PEA used in the composition is present in the combination of suitable solubilizer or bioenhancer to enhance the solubility and bioavailability of poorly water soluble PEA, the efficacy of micronized PEA is improved under optimum condition by using bioenhancer that is collectively termed as Bio-optimized PEA.

In an additional embodiment, the micronized PEA can be incorporated in micelles, encapsulation or complex.

It may be noted that peripheral and/or central immune cell participation is a key element of the molecular processes associated with chronic pain; therefore the modulation of these cells' activation is indeed efficacious in chronic pain independent of etiopathogenesis.

In this regard the present remedy includes the bioactive agent(s) that targets mast cell activation. In particular, mast cells organise inflammatory responses in peripheral nervous tissues, with microglia doing the same in spinal cord. Thus, the present combination therapy targets complementary pathways or mechanisms results in more efficacious pain relief, especially in those cases that are refractory to standard therapy which acts only on neurons.

PEA ensures important role with activated mast cells to what it does with over-activated neurons.

PEA reduces mast cell migration and degranulation and can shift them from their activated to their resting states.

Further it is reported that immune responses are mainly dependent on immune cells (like mast cells, microglia, neutrophils, macrophages, Schwann cells, and T cells) and some of their inflammatory mediators. In a normal state, mast cells have granules that contain a variety of bioactive chemicals. Nervous injury triggers neuroinflammation, which activates mast cells, and activated mast cells in turn release inflammatory factors, such as bradykinin, prostaglandins, histamine, and substance P. The neuropathic pain induces mast cell activation and degranulation and neutrophil and macrophage infiltration, which is reversed by treatment with a mast cell stabilizer. Therefore mast cells are powerful neuropathic pain mediators.

Microglia, which are glial cells that are located throughout the CNS, become activated in response to nerve injury and immunological stimuli, including proinflammatory signals released from immune cells, such as mast cells. This interaction between mast cells and microglia regulates peripheral pain signaling. Microglia activation causes pain states by releasing proinflammatory cytokines, chemokines, and proteases. Astrocytes, the most abundant glial cell type in the CNS, also play a major role in pain facilitation and are fundamental contributors to the neuropathic pain involved in neuroinflammation. Therefore, a promising therapeutic target for managing neuropathic pain would be factors that mediate mast and glia cell reactivity.

The efficacy of PEA in this group confirms that its actions are independent from those of other therapies and confirms that the concomitant control of mast cell activity in the periphery and microglia activation in the CNS significantly reduce the intensity of neuropathic pain.

Particularly PEA inhibits mast cell, glia and astrocyte activation, as well as NGF-related inflammation cascades to get relief from nerve sensation.

In another embodiment, the synergistic composition comprises therapeutically effective amount of PEA or pharmaceutically/nutraceutically acceptable salts thereof, wherein PEA is present in the range of 1-500 mg, preferably in the range of 5-450 mg of total composition.

In another embodiment, the invention discloses synergistic effect of nitric oxide for reducing pain through vasodilation of poorly perfused nerves and restores their normal function.

Nitric Oxide (NO) is an unstable free-radical gas which reacts rapidly with oxygen to form nitrogen oxides. Water soluble, NO is produced normally in numerous tissues and is considered to be a mediator of cell-to cell communication; it functions in numerous processes including vasodilation, inflammation, and neurotransmission.

It may be noted that nerves have a normal membrane potential maintained by ion (potassium and sodium) pumps that derive energy from the synthesis of ATP. However, compromised circulation, causes nerves to malfunction, due in part to the absence of normal amounts of oxygen and nutrients (such as glucose), which together synthesize ATP. Lack of adequate oxygen and nutrients, and the lower synthesis of ATP, adversely affects normal membrane potential. Poor circulation to the nerves prevents them from sending the appropriate signals (for pressure and temperature) to the brain and that causes pain. NO mediated vasodilation enhances delivery of oxygen and nutrients to poorly perfused nerves to re-establish their normal membrane potential.

Lundberg, Jon O., et al. has reported that inorganic nitrate rich food is a potential source for systemic generation of nitric oxide [*Free Radic Biol Med.* 2004, vol. 37, p. 395-400].

It may be noted that there are two known pathways for NO production in the human body. The first is the endogenous pathway, where l-arginine is converted to NO by nitric oxide synthases (NOS). The second pathway is the exogenous pathway, which comprises consumption of nitrate rich food.

After ingestion of nitrate rich vegetables, ($NO3^-$) nitrate gets absorbed into circulation, undergoes salivary bacterial reduction to nitrite ($NO2^-$) and then to nitric oxide (NO) this nitric oxide formation supports vasodilation and enhances delivery of oxygen and nutrients to poorly perfused nerves. This pathway is also known as $NO3^-$-$NO2^-$-NO reduction pathway.

The administration of inorganic nitrate/nitrate rich food follows exogenous reduction pathway and leads to enchantment of the bioavailability of cellular nitric oxide.

In yet another embodiment, the vegetables enriched with inorganic nitrate can be selected from Class I, Class II, Class III, Class IV and Class V; preferably the inorganic nitrate is sourced from Class V vegetables such as red beetroot, red spinach and like thereof.

The classification of vegetables according to inorganic nitrate content (mg/100 gm fresh weight) is given in Table 1, as below:

TABLE 1

| | |
|---|---|
| Class I (<20) | Artichoke, asparagus, broad bean, Brussels sprouts, eggplant, garlic, onion, green bean, mushroom, pea, pepper, potato, squash, tomato |
| Class II (20 to <50) | Broccoli, carrot, cauliflower, cucumber, pumpkin, chicory |
| Class III (50 to <100) | Cabbage, dill, turnip, Savoy cabbage |
| Class IV (100 to < 250) | Celeriac, Chinese cabbage, endive, escarole, fennel, kohlrabi, leaf chicory, leek, parsley |
| Class V (>250) | Celery, chervil, cress, Lamb's lettuce, lettuce, radish, red beetroot, rocket (rucola), spinach, Swiss chard |

In yet another embodiment, the pharmaceutically acceptable compositions of the invention include, but are not limited to, inorganic nitrite, e.g., a salt or ester of nitrous acid ($HNO_2$), or a pharmaceutically acceptable salt thereof. Nitrite salts can include, without limitation, salts of alkali metals, e.g., sodium, potassium; salts of alkaline earth metals, e.g., calcium, magnesium, and barium; and salts of organic bases, e.g., amine bases and inorganic bases.

In addition to sodium nitrite, representative inorganic nitrite compounds include: ammonium nitrite ($NH_4NO_2$), barium nitrite ($Ba(NO_2)_2$; e.g., anhydrous barium nitrite or barium nitrite monohydrate), calcium nitrite ($Ca(NO_2)_2$; e.g., anhydrous calcium nitrite or calcium nitrite monohydrate), cesium nitrite ($CsNO_2$), cobalt(II) nitrite ($Co(NO_2)_2$), cobalt(III) potassium nitrite ($CoK_3(NO_2)_6$; e.g., cobalt(III) potassium nitrite sesquihydrate), lithium nitrite ($LiNO_2$; e.g., anhydrous lithium nitrite or lithium nitrite monohydrate), magnesium nitrite ($MgNO_2$; e.g., magnesium nitrite trihydrate), potassium nitrite ($KNO_2$), rubidium nitrite ($RbNO_2$), silver(I)nitrite ($AgNO_2$), strontium nitrite ($Sr(NO_2)_2$), and zinc nitrite ($Zn(NO_2)_2$).

The nitrite compounds of the present invention can be prepared in a variety of ways known to person of ordinary skill in the art of chemical synthesis. Methods for preparing nitrite salts are well known in the art and a wide range of precursors and nitrite salts are readily available commercially.

In further embodiment, the synergistic composition comprises therapeutically effective amount of inorganic nitrate or nitrite salts, wherein inorganic nitrate or nitrite either alone or in combination may be present in the range of 1-100 mg, preferably in the range of 1-80 mg of total composition.

In yet another preferred embodiment, the invention relates to synergistic nutritional compositions comprising combination of PEA present in the range of 1 to 500 mg and inorganic nitrate/nitrite present in the range of 1 to 100 mg along with pharmaceutically acceptable excipients/carriers.

Particularly, the invention relates to synergistic nutritional compositions comprising combination of PEA which is present in the range of 5 to 450 mg and inorganic nitrate/nitrite present in the range of 1 to 80 mg, along with pharmaceutically acceptable excipients/carriers.

In one embodiment, the invention provides value added inorganic nitrate obtained from natural source; particularly nitrate is obtained from standardized red spinach (*Amaranthus*) extract. The nitrate content is not less than 9.0%.

The term 'standardized' refers to the value added product where nitrate content is enriched with the process under generally acceptable guidelines for standard substances.

In yet another embodiment, the invention provides red spinach extract which is present in the range of 50 to 500 mg, preferably 100 to 300 mg, wherein the extract contains inorganic nitrate in the range of 5 to 50 mg of total extract.

Red spinach is a member of the plant family Amaranthaceae, which includes nearly 2,500 species ranging from spinach to beetroot to grains such as amaranth and quinoa. The *Amaranthus* genus comprising species such as *Amaranthus caudatus, Amaranthus cruentus, Amaranthus tricolor, Amaranthus blitum, Amaranthus viridis, Amaranthus dubius, Amaranthus hypochondriacus, Amaranthus hybridus* or like thereof.

In the present invention the preferable *Amaranthus* species is *Amaranthus cruentus*; wherein the leaves of the plant are extracted by known method to get extract enriched with nitrate content (NLT 9.0%); preferably containing 9.24% of nitrate on dried basis. Further the specific breed of *Amaranthus cruentus* is developed and cultivated in India.

*Amaranthus cruentus* has several common names, including blood amaranth, red amaranth, purple amaranth, prince's feather, Mexican grain amaranth, Amaranth, African spinach, Indian spinach.

In further embodiment, the invention provides the nutrition composition comprising standardized red spinach (*Amaranthus*) extract containing more than 9.0% of nitrate; preferably 9.0% to 12.0%, more preferably 9.10 to 9.80%.

In some embodiment the invention provides the nutrition composition comprising standardized red spinach (*Amaranthus*) extract containing 9.24% of inorganic nitrate content.

In one more embodiment, the invention offers nutritional composition comprising synergistic blend/combination of PEA and red spinach extract enriched with nitrate content, when administered in suitable dosage form gives significant results in pain treatment without any adverse effect.

The active ingredients PEA is in micronized form where pharmaceutically acceptable solubilizers and bioenhancers are added under optimize condition to get PEA with improved bioavailability and efficacy.

In one preferred embodiment, the invention provides synergistic pain relieving nutritional composition comprising combination of PEA and standardized red spinach extract having enriched nitrate content, present in the ratio of 1:0.1 to 1:5, particularly 1:0.2 to 1:2 along with pharmaceutically acceptable excipients.

Moreover, the composition comprising synergistic exogenous blend of PEA and standardized red spinach extract enriched with nitrate content, wherein nitrate content is NLT 9.0%, particularly 9.0% to 12.0%.

In yet another embodiment, the invention provides synergistic nutritional composition, comprising PEA and inorganic nitrate of red spinach extract are present in the ratio of 1:0.01 to 1:0.5; preferably 1:0.02 to 1:0.2.

In another embodiment, the composition comprising micronized, highly bioavailable and soluble form of PEA, which is present in the range of 40-80% by weight of total composition.

In yet another embodiment, the composition comprising standardized red spinach extracts which is preferably *Amaranthus cruentus* extract, present in the range of 10-50% by weight of total composition.

The *Amaranthus cruentus* dried leaves are treated with solvent and dried by conventional method to get value added nitrate enriched powder. Particularly it is aqueous extract of *Amaranthus cruentus* dried leaves.

In further embodiment, the composition comprising red spinach extract is enriched with nitrate content, wherein the nitrate content is NLT 9.0%, and the overall nitrate content present in the composition is in the range of 1.0 to 5.0% by weight of total composition.

The term 'pain management' can be also referred as 'pain medicine', 'pain control' or 'algiatry' which comprises a number of methods to prevent, reduce, or stop pain sensations. These include the use of medications; physical methods and psychological methods.

In another embodiment, the invention relates to synergistic nutritional composition which is useful for treating pain or pain related disorders, particularly neuropathic pain, and more particularly diabetic peripheral neuropathy (DPN).

In one preferred embodiment, the invention provides a synergistic nutritional composition for treating neuropathic pain comprising a therapeutic blend of PEA and standardized red spinach extract enriched with nitrate content wherein the PEA and standardized red spinach extract enriched with nitrate content are present in the ratio of 1:0.1 to 1:5, along with pharmaceutically acceptable excipients.

In one preferred embodiment, the invention provides method of treating neuropathic pain in a subject in need thereof, wherein the method comprising, administering to the subject a therapeutically effective amount of nutritional composition comprising exogenous synergistic blend of palmitoylethanolamide (PEA) and standardized red spinach extract enriched with nitrate content, wherein (PEA) and standardized red spinach extract are present in the ratio of 1:0.1 to 1:5 along with pharmaceutically acceptable excipients.

In another preferred embodiment, the invention provides a method of treating neuropathic pain in a subject in need thereof, wherein the method comprising, oral administration of therapeutically effective amount of a nutritional composition comprising exogenous synergistic blend of palmitoylethanolamide (PEA) and standardized red spinach extract enriched with nitrate content, wherein the PEA and the standardized red spinach extract enriched with nitrate content are present in the ratio of 1:0.2 to 1:2; and PEA and nitrate of red spinach extract are present in the ratio of 1:0.02 to 1:0.2, along with pharmaceutically acceptable excipients.

In another embodiment, the red spinach extract enriched with nitrate content comprises inorganic and organic nitrate but more preferably nitrate content is enriched with inorganic nitrate.

Diabetic peripheral neuropathy caused by microangiopathy affects nutrient and oxygen supply to neurons. This results in degeneration of neurons and inflammation causing severe neural pain. According to the invention PEA exhibits anti-inflammatory effect that attenuates the nerve pain, where dietary inorganic nitrate improves endogenous nitric oxide dependent vasodilatation and thus ameliorate oxygen and nutrient supply to ailing neurons & helps in regeneration.

Small fiber neuropathy is a type of peripheral neuropathy. Small fiber neuropathy occurs when the small fibers of the peripheral nervous system are damaged. Small fibers in the skin relay sensory information about pain and temperature. In the organs, these small fibers regulate automatic functions such as heart rate and breathing.

Peripheral neuropathies affect the peripheral nervous system. This includes the nerves outside of the brain and spinal cord. With small fiber neuropathy, the narrow nerve fibers of the peripheral nervous system are affected. Small fiber neuropathy can be the first sign of an underlying condition, such as diabetes.

Small fiber neuropathy is considered a form of peripheral neuropathy because it affects the peripheral nervous system, which connects the brain and spinal cord to muscles and to cells that detect sensations such as touch, smell, and pain.

It is noteworthy that the present synergistic composition not only reduces inflammation but also improves functioning of neurons by activating e-NOS expression.

In diabetic peripheral nerve there are apparent physiological deficits in nitric oxide vasodilation of vasa nervorum that may account for functional microangiopathy. The localization of eNOS in endothelial cells makes it a more direct target of diabetic complications. In response to such abnormalities, one might expect endothelial cells in diabetic nerve or ganglia to compensate by increasing their synthesis of eNOS or by increasing its activity [Adv Pharmacol 1995; 34:215-34].

In some embodiment, the present nutritional composition enriched with inorganic nitrate content ameliorates eNOS expression in microvascular endothelial cells.

The term "neuropathic pain" as used herein has its conventional meaning and has been defined by the International Association for the Study of Pain (IASP, 2011) as 'pain caused by a lesion or disease of the somatosensory nervous system'. The IASP further specifies: 'Neuropathic pain is a clinical description (and not a diagnosis) which requires a demonstrable lesion or a disease that satisfies established neurological diagnostic criteria'. The presence of symptoms or signs (e.g., touch-evoked pain) alone does not justify the use of the term neuropathic. Some disease entities, such as trigeminal neuralgia, are currently defined by their clinical presentation rather than by diagnostic testing. Other diagnoses such as post-herpetic neuralgia are normally based upon the history.

Neuropathic pain can be divided according to the IASP in two different pain states:
1. Central neuropathic pain, defined by the IASP as 'pain caused by a lesion or disease of the central somatosensory nervous system'; and
2. Peripheral neuropathic pain, defined by the IASP as 'pain caused by a lesion or disease of the peripheral somatosensory nervous system'.

Further the neuropathic pain including DPN refers to a situation when diagnostic investigations (e.g. imaging, neurophysiology, biopsies, lab tests) reveal an abnormality or trauma.

Further neuropathic pain can take a variety of forms depending on its origin and can be characterized as acute, subacute, or chronic depending on the duration.

In certain embodiments, the neuropathic pain is diabetic peripheral neuropathy, small fiber neuropathy, post-herpetic neuralgia, trigeminal neuralgia, phantom limb pain, carpal tunnel syndrome, sciatica, pudendal neuralgia, complex regional pain syndrome, sensory polyneuropathies, mononeuropathies, or central pain syndrome, headaches, joint pain, backaches, sinus pain, muscle pain, nerve pain, and pain affecting specific parts of the body, such as shoulders, pelvis, and neck, and/or pain that is associated with lower back pain, lumbopelvic pain, arthritis, headache, multiple sclerosis, fibromyalgia, shingles, nerve damage, cancer, a demyelinating neuropathy, chemotherapy induced neuropathy, HIV neuropathy, post herpetic neuropathy or postoperative pain.

In further embodiment, the invention provides synergistic nutritional composition for treating neuropathic pain, which is caused due to spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, metabolic disorders, hereditary conditions, infections, vasculitis and autoimmune diseases, central nervous system pain, such as pain due to spinal cord or brain stem damage, cerebrovascular accidents, tumors, infections, demyelinating diseases including multiple sclerosis, low back pain, sciatica, and post-operative.

In some embodiment, the pain management relates to control neuropathic pain particularly prevention of diabetic peripheral neuropathy at early stage by targeting the endothelial cells responsible for Endothelial dysfunction. Dysfunction of the endothelium in diabetes mellitus is characterized by changes in proliferation, barrier function, adhesion of other circulating cells, sensitivity to apoptosis, changes in angiogenic and synthetic properties of endothelial cells [*Blood.* 1998 May 15; 91(10):352 7-61].

According to one embodiment, the treatment involves consumption of effective dosage of present nutritional composition through any route of administration, but preferably oral administration.

An "effective amount of nutrients" is an amount sufficient to prevent, treat, reduce, and/or ameliorate the symptoms and/or underlying causes of pain or pain related disorders, like diabetic peripheral neuropathy.

In the context of the present invention, the term "treatment" and the like refer to alleviate, slow the progression, prophylaxis, attenuation, or cure of existing pain. The instant composition is used for treating pain or pain related disorder in a subject in need thereof, means either the administration of the remedy to prevent the onset or occurrence of pain, or to treat existing cause of pain.

In the context of the present invention, the terms "treatment" and the like refer to alleviate, mitigate, prophylaxis, attenuate, manage, regulate, modulate, control, minimize, lessen, decrease, down regulate, up regulate, improve, moderate, prevent, inhibit, stabilize, ameliorate or cure, heal the indications of neuropathic pain.

The treatment further includes delaying or reversing or preventing or reducing the development or progression or formation or occurrence of conditions or indications related to neuropathic pain.

The 'subject in need thereof' pertains to subject preferably mammal, more preferably human suffering from pain or pain related disorder or in a subject to prevent occurrence of pain, particularly neuropathic pain, more particularly diabetic peripheral neuropathy.

The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. Further, a "therapeutically effective" amount is an amount that reduces the risk, potential, possibility or occurrence of a disease or disorder, or provides some alleviation, mitigation, and/or reduction of at least one indicator (e.g., blood or serum CRP level), and/or decrease in at least one clinical symptom of a disease or disorder (e.g., pain such as neuropathic pain as disclosed herein).

Moreover the term "specific or effective amount" is intended to mean the therapeutically effective dose of instant bioactive compounds namely m-PEA and standardized red spinach extract enriched with IN in combination to give significant therapeutic efficacy, which is otherwise not obtained by use of single ingredient of the composition.

In another embodiment, the invention relates to synergistic nutritional composition which can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Particularly the composition can be administered to subject in a form suitable for oral use, such as a tablet, capsule (in the form of delayed release, extended release, sustained release, enteric coated release); aqueous or oily solution, suspension or emulsion; for topical including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet or capsule, film or for parenteral use (including intravenous, subcutaneous, intramuscular, intravascular or infusion), such as a sterile aqueous or oil solution or suspension.

The term "pharmaceutically acceptable salt" refers to a salt prepared from pharmaceutically acceptable non-toxic acids or bases, halides, sulphates, phosphates, nitrate, metal ions, minerals, chelates, complex, esters, oxide, amines which are well known in the art.

As used herein, the term "pharmaceutically acceptable carriers/vehicles/diluents or excipients" is intended to mean, without limitation, any adjuvants, carriers, excipients, sweetening agents, diluents, preservative, dye/colorants, flavor enhancers, surfactants, wetting agents, dispersing agents, suspending agents, complexing agents, stabilizers, isotonic agent, solvent, emulsifier, encapsulating agent, polymers, coating agent, wax, encapsulating polymeric delivery systems. Excipients may also include, antiadherents, antioxidants, binders, pH-modifier, solvents, coatings, compression aids, disintegrants, emollients, fillers (diluents), film formers, fragrances, glidants (flow enhancers), lubricants, preservatives, sorbents, anticaking agent, food additives, or waters of hydration.

In some embodiment of the invention, the diluents are selected from starches, hydrolyzed starches, and partially pregelatinized starches, anhydrous lactose, cellulose powder, lactose monohydrate, and sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, corn starch, pregelatinized starch, dextrin, β-cyclodextrin, dextrates, dextrose, erythritol, ethylcellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the amount of diluent in the pharmaceutical composition/formulation is present in the range of 1% to 40% by wt. of the total composition/formulation.

In further embodiment, the binder is selected from disaccharides such as sucrose, lactose, polysaccharides and their derivatives like starches, cellulose or modified cellulose such as microcrystalline cellulose and cellulose ethers such as hydroxypropyl cellulose (HPC); hydroxypropyl methyl cellulose (HPMC); sugar alcohols such as xylitol, sorbitol or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethylcellulose, guar gum, hydrogenated vegetable oil, mineral oil, hydroxyethyl cellulose, hydroxymethyl cellulose hydroxyl ethylmethyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methyl-cellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colourants and wax.

In some embodiment of the invention, the amount of binder in the pharmaceutical composition/formulation is present in the range of 0.1% to 20% by wt. of the composition/formulation.

Further according to the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like.

In some embodiment of the invention, the amount of lubricant in the pharmaceutical composition/formulation is present in the range of 0.1% by wt. to 5% by wt. of the total composition/formulation.

In some embodiment, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, magnesium silicate, magnesium trisilicate, silicon dioxide or the like.

In some embodiment of the invention, the amount of glidant present in the pharmaceutical composition/formulation ranges from 0.1% by wt. to 5% by wt. of the total composition/formulation.

In some embodiment, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In some embodiment of the invention, the amount of solvent in the pharmaceutical composition/formulation is used in a quantity sufficient to 100% by wt. of the composition/formulation.

The additional additives include polymer, a plasticizer, a sweetener, and a powdered flavor, preservative, colorant, surfactant and other excipients. The powdered flavor composition includes a flavourant associated with a solid carrier, coating materials are used, for example synthetic polymers, shellac, corn protein zein or other polysaccharides, gelatin, fatty acids, waxes, shellac, plastics, and plant fibers and like thereof. The additives are used in the range of 1 to 20% w/w of unit dose.

Further the surfactant is selected from anionic surfactants such as Sulfate, sulfonate, and phosphate esters or cationic surfactants such as quaternary ammonium salts, benzalkonium chloride or zwitterionic surfactants or non-ionic surfactants or fatty acid esters or biosurfactants or mixtures thereof, which are present in the range of 0.1 to 5% w/w of unit dose.

Notably, the instant synergistic composition is non-hazardous, non-toxic and safe for human consumption without any side effects, therefore the instant composition can also be used under preventive therapy in healthy subjects.

The present nutritional composition is used to manage pain conditions in the subject in need thereof, means the administration of the remedy either to prevent occurrence or for pre-existing cause of neuropathic pain such as DPN.

In another embodiment, the invention provides a method of treating a subject suffering from neuropathic pain disorders or diseases, the method comprising administering to the subject an effective amount of the present synergistic nutritional composition to alleviate nerve pain sensation and inflammation thereof.

The 'subject in need thereof' pertains to subject preferably mammal, more preferably human having pre-existing or onset symptoms of neuropathic pain, like DPN.

The subject may be healthy person which can use the composition under preventive therapy.

In some embodiments, the invention provides method of treating neuropathic pain by administering the present synergistic nutritional composition comprising combination of m-PEA and standardized red spinach extract enriched with nitrate content present in the ratio of 1:0.1 to 1:1.

The term "pharmaceutical composition," as used herein, represents a composition containing a compound described herein (e.g., inorganic nitrite, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

In therapeutic applications, compositions can be administered to a patient suffering from pain (e.g., neuropathic pain, neuropathy, diabetic peripheral neuropathy) in an amount sufficient to relieve the symptoms of pain like discomfort, soreness, tightness, stiffness, fatigue, sleeplessness, weakened immune system, depression, anxiety, stress, irritability, or disability.

The dosage is likely to depend on such variables as the type and extent of progression of the pain (e.g., as determined by the "Pain Ladder" guideline from the World Health Organization), the severity of the pain (e.g., acute, subacute, or chronic), the age, weight and general condition of the particular patient, the relative biological efficacy of the composition selected, formulation of the excipient, the route of administration, and the judgment of the attending clinician.

An effective dose is a dose that produces a desirable clinical outcome by, for example, improving a sign or symptom of pain or slowing its progression. Accordingly the effective unit dose can be formulated in the range of 100 to 1000 mg, preferably 400-1000 mg and administered daily once or twice or thrice based on the intensity of the pain.

Further, the instant synergistic nutritional composition can be administered to subject in need thereof, in a form suitable for oral use, such as a tablet, capsule (in the form of delayed release, extended release, sustained release, enteric coated release); hard gelatin capsules, soft gelatin capsules in an oily vehicle, granulate for sublingual use, effervescent tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, as tablets, pellets, granules, capsules, lozenges, aqueous or oily solutions, suspensions, emulsions, sprays or reconstituted dry powdered form with a liquid medium or syrup; for topical use including transmucosal and transdermal use, such as a cream, ointment, gel, aqueous or oil solution or suspension, salve, parch or plaster; for nasal use, such as a snuff nasal spray or nasal drops; for vaginal or rectal use, such as a suppository; for administration by inhalation, such as a finely divided powder or a liquid aerosol; for sub-lingual or buccal use, such as a tablet or capsule, film. Further the composition can be formulated for parenteral use including intravenous, subcutaneous, intramuscular, intravascular, infusion, intraperitoneal, intracerebral, intracerebroventricular, or intradermal.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

The invention may be further illustrated by the following examples, which are for illustrative purposes only and should not be construed as limiting the scope of the invention in anyway.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes or alterations which come within the ambit of equivalency are intended to be encompassed therein.

EXAMPLES

Example 1

| Composition 1a: Synergistic Blend | |
|---|---|
| Ingredient | w/w % |
| Bio-Optimized PEA | 40-80% |
| Standardized Red Spinach Extract (*Amaranthus cruentus*) (with nitrate content NLT 9.0%) | 10-50% |

| Composition 1b: Synergistic Blend | |
|---|---|
| Ingredient | w/w % |
| Bio-Optimized PEA | 60 ± 5% |
| Standardized Red Spinach Extract (*Amaranthus cruentus*) (with nitrate content NLT 9.0%) | 40 ± 5% |

| Composition 1c: Synergistic Blend | |
|---|---|
| Ingredient | w/w % unit dose |
| Bio-Optimized PEA | 75 ± 5% |
| Standardized Red Spinach Extract (*Amaranthus cruentus*) (with nitrate content NLT 9.0%) | 25 ± 5% |

The proprietary blend PALMEIN™ contains Bio-Optimized™ PEA 40-80%+Standardized Red Spinach Extract 10-50% (with nitrate content NLT 9.0%).

The therapeutic proprietary blend with proportionate excipients is filled in soft gel, hard gel, veg capsule by known techniques. Further the blend with the proportionate excipients is compressed to get tablet in coated or uncoated form.

| Composition 2: Tablet/Capsule | |
|---|---|
| Ingredient | w/w % unit dose |
| Bio-Optimized PEA | 45 ± 8% |
| Standardized Red Spinach Extract (*Amaranthus cruentus*) (with nitrate content 9.24%) | 30 ± 5% |
| Excipient | 15 ± 5% |
| Average Wt | 100% |
| Average wt in mg | 600-700 mg |

| Composition 3: Tablet/Capsule | |
|---|---|
| Ingredient | w/w % unit dose |
| Bio-Optimized PEA | 55 ± 8% |
| Standardized Red Spinach Extract (*Amaranthus cruentus*) (with nitrate content 9.24%) | 20 ± 5% |
| Excipient | 20 ± 5% |
| Average Wt | 100% |
| Average wt in mg | 500-580 mg |

| Composition 4: Tablet/Capsule | |
|---|---|
| Ingredient | w/w % unit dose |
| Bio-Optimized PEA | 46-52% |
| Standardized Red Spinach Extract (*Amaranthus cruentus*) (with nitrate content 9.24%) | 30-35% |
| Diluent | 1-10% |
| Binder | 0.5-5% |
| Glidant | 0.5-5% |
| Lubricants | 0.5-5% |
| Additives | 1-10% |
| Solvent | QS |

| Composition 5: Tablet/Capsule | |
|---|---|
| Ingredient | w/w % unit dose |
| Bio-Optimized PEA | 54-62% |
| Standardized Red Spinach Extract (*Amaranthus cruentus*) (with nitrate content 9.24%) | 16-22% |
| Diluent | 1-20% |
| Binder | 0.5-5% |
| Glidant | 0.5-5% |
| Lubricants | 0.5-5% |
| Additives | 1-10% |
| Solvent | QS |

| Composition 6: Tablet/Capsule | |
|---|---|
| Ingredient | mg per unit dose |
| Bio-Optimized PEA | 300 |
| Standardized Red Spinach Extract (*Amaranthus cruentus*) (with nitrate content 9.24%) | 206 |
| Microcrystalline Cellulose | 2-20 |
| Silicon dioxide | 5-15 |
| Hydroxypropyl Methylcellulose | 2-10 |
| Zinc Stearate | 2-10 |
| PVP K-30 | 5-10 |
| Talc | 1-10 |
| Polysorbate 80 | 5-20 |
| Manitol | 5-20 |
| Propylene Glycol | QS |
| Water | QS |
| Average weight | 600-700 mg |

The blend in this composition is referred to as PALMEIN™ 506

| Composition 7: Tablet/Capsule | |
|---|---|
| Ingredient | mg per unit dose |
| Bio-Optimized PEA | 300 |
| Standardized Red Spinach Extract (*Amaranthus cruentus*) (with nitrate content 9.24%) | 103 |
| Microcrystalline Cellulose | 2-20 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Manitol | 5-20 |
| IPA | QS |
| Water | QS |
| Average weight | 500-580 mg |

The blend in this composition is referred to as PALMEIN™ 403

The present composition is stable for 06 months under the accelerated condition [40° C., 75% RH], where the purity of the active ingredients is above 95%.

Example 2

Animal Study—Evaluation of analgesic potential of the test substances against tail immersion model in experimental mice.
Test System and Animal Husbandry
Species: Mice
Strain: Swiss albino; Sex: Male
No. of animals: 30 Animals (n=6 per group)
Body weight: 30-35 gm
CPC SEA Registration Number—1803/PO/RcBi/S/2015/CPCSEA
Animal House Conditions
Lighting: 12/12 hour light-dark cycle
Temperature: 22±3° C.
Relative Humidity: 30 to 70%
Animals had continuous access to fresh, potable, uncontaminated drinking water.
Feed: Normal chow diet
Group, Designation and Dose Levels:

TABLE 2

Animal grouping and treatment details

| Group | Treatment | Dose | No. of Animals |
|---|---|---|---|
| G1 | Pain Control | Normal saline | 6 |
| G2 | Bio-optimized PEA | 739.8 mg/kg | 6 |
| G3 | Red Spinach Extract (*Amaranthus cruentus*) (enriched with Inorganic nitrate) | 16.43 mg/kg | 6 |
| G4 | Composition 1a | 739.8 mg/kg: 16.43 mg/kg | 6 |
| G5 | Pregabalin (LYRICA® 75 mg) | 20 mg/kg | 6 |

Experimental Procedure

Male Swiss albino mice weighing between 30-35 g were used. Mice were placed into individual cylindrical mice holders leaving the tail hanging out freely. The animals were allowed to get acclimatized to mice holders for 30 min before testing. The lower 5 cm portion of the tail was marked. This part of the tail was immersed in a cup of freshly filled water at 55° C. The reaction time was recorded using a stop-watch. After each determination the tail was carefully dried. The reaction time was determined before and periodically 0 min, 30 min, 60 min, 90 min, 120 min, 180 min and 240 min after the oral administration of test substance. The cut off time of immersion was 15 second. The percentage maximum possible effect (% MPE) was calculated using the following formula:

[(Post drug latency-Pre drug latency)/(15-Pre drug latency)]×100.

The values were expressed in Mean±SEM. The significance of in vivo data was analyzed by One way anova followed by Dunnet test. P<0.05 was considered as statistically significant.

Results

TABLE 3

Body weight of experimental animals

| Group | Treatment | Body weight (gms) |
|---|---|---|
| G1 | Pain Control | 31.42 ± 0.37 |
| G2 | P$_3$A | 32.20 ± 0.52 |
| G3 | P$_3$B | 30.50 ± 0.32 |
| G4 | P$_3$A:P$_3$B | 31.58 ± 0.44 |
| G5 | Pregabalin (LYRICA ® 75 mg) | 30.87 ± 0.37 |

TABLE 4

Modulatory effect of test substances on Tail Immersion Latency reaction time (Seconds)
TAIL IMMERSION LATENCY REACTION TIME (Seconds)

| Group | Treatment | 0 Min (Sec) | 30 Min (Sec) | 60 Min (Sec) | 90 Min (Sec) | 120 Min (Sec) | 180 Min (Sec) | 240 Min (Sec) |
|---|---|---|---|---|---|---|---|---|
| G1 | Pain Control | 2.67 ± 0.21 | 2.67 ± 0.21 | 2.50 ± 0.22 | 2.33 ± 0.21 | 2.67 ± 0.21 | 2.50 ± 0.22 | 2.67 ± 0.21 |
| G2 | P$_3$A | 2.50 ± 0.22 | 5.17 ± 0.31* | 5.83 ± 0.31* | 6.50 ± 0.22* | 7.50 ± 0.22* | 8.33 ± 0.33* | 7.50 ± 0.22* |
| G3 | P$_3$B | 2.67 ± 0.21 | 5.83 ± 0.17* | 6.50 ± 0.22* | 7.17 ± 0.17* | 8.00 ± 0.37* | 8.83 ± 0.31* | 7.83 ± 0.31* |
| G4 | P$_3$A:P$_3$B | 2.67 ± 0.21 | 6.17 ± 0.31* | 7.00 ± 0.37* | 7.67 ± 0.56* | 8.83 ± 0.48* | 9.33 ± 0.21* | 8.33 ± 0.33* |
| G5 | Pregabalin (LYRICA ®) 75 mg | 2.50 ± 0.22 | 6.17 ± 0.40* | 7.67 ± 0.21* | 8.50 ± 0.22* | 9.33 ± 0.42* | 9.83 ± 0.48* | 9.00 ± 0.37* |

*Values were expressed as Mean ± SEM

TABLE 5

Effect of Test substances on percentage maximum possible effect
PERCENTAGE MAXIMUM POSSIBLE EFFECT

| Group | Treatment | 0 Min (%) | 30 Min (%) | 60 Min (%) | 90 Min (%) | 120 Min (%) | 180 Min (%) | 240 Min (%) |
|---|---|---|---|---|---|---|---|---|
| G1 | Pain Control | — | — | — | — | — | — | — |
| G2 | P$_3$A | — | 21.33 | 26.67 | 32.00 | 40.00 | 46.67 | 40.00 |
| G3 | P$_3$B | — | 25.68 | 31.08 | 36.49 | 43.24 | 50.00 | 41.89 |
| G4 | P$_3$A:P$_3$B | — | 28.38 | 35.14 | 40.54 | 50.00 | 54.05 | 45.95 |
| G5 | Pregabalin (LYRICA ®) 75 mg | — | 29.33 | 41.33 | 48.00 | 54.67 | 58.67 | 52.00 |

DISCUSSION

In the present study analgesic activity was evaluated by tail immersion model.

Table-4 shows the tail immersion latency reaction time after the administration of tests substance at different time interval. P$_3$A (G2), P$_3$B (G3) and the combination of P$_3$A+P$_3$B (G4) and Pregabalin (LYRICA®) (G5) treated groups showed significant increased tail immersion latency reaction time when compared with Pain control group (G1). P$_3$A (G2), P$_3$B (G3) and the combination of P$_3$A+P$_3$B (G4) and Pregabalin (G5) treated groups showed significant increased percentage maximum possible effect when compared with Pain control (G1) group at different intervals of time. P$_3$A+P$_3$B (G4) (54.05%) and Pregabalin (G5) (58.67%) showed better percentage maximum possible effect at 180 Min when compared with P$_3$A (G2) (46.67%) and P$_3$B (G3) (50.00%).

Conclusion: Overall result concluded that the combination of P$_3$A+P$_3$B (G4) showed better analgesic activity than individual test substance P$_3$A (G2) and P$_3$B (G4). The composition exhibits better and improved analgesic potential over control.

Example 3

Modulatory Effect of the Test Substances on eNOS Gene by Gene Expression Method

The test substances were evaluated for its gene expression activity in H9C2 (rat cardiomyocytes), the concentration of test substances (G2, G3 and G4,) is 500 μg/ml were taken for gene expression studies. In gene expression study the test substance, at higher concentration showed up-regulation in the level of eNOS gene as compared to the control tissue. [Hunter C. Champion, et al., PNAS, 2005; 102:5:1661-1666.]

Method

Outline of the Method eNOS were estimated for the test substance by gene expression method, where the level of expression of eNOS expression on Human Cardiomyocytes (H9C2) was determined with respect to untreated H9C2 cells.

RNA Isolation and cDNA Synthesis

The H9C2 cells treated with test samples were subjected to cell lysis by treating with Tri-extract reagent. Chloroform was added, to isolate the total RNA from the sample and subjected for centrifugation. Out of the three distinct layers observed, upper layer was collected in fresh tube and equal volume of isopropanol was added and incubated at –200° C. for 10 mins. After the incubation followed by centrifugation, appropriate volume of ethanol was added to resuspend the pellet. After incubation and centrifugation, the pellet was air dried and appropriate volume of TAE buffer was added. The isolated total RNA was further used for cDNA synthesis. cDNA was synthesized by priming with oligo-dT primers followed by reverse transcriptase enzyme treatment according to manufacturer's protocol (Thermoscientific). The cDNA thus synthesized was taken up for PCR for the amplification of eNOS and GAPDH (internal control).

RT-PCR Procedure

The mRNA expression levels of eNOS were determined using semi-quantitative reverse transcriptase-polymerase chain reaction (RT-PCR). 50p of the reaction mixture was subjected to PCR for amplification of eNOS. cDNAs using specifically designed primers procured from Eurofins, India and as an internal control GAPDH/3-Actin (House-keeping genes) was co-amplified with each reaction.

Amplification Conditions for eNOS Gene eNOS: 95° C. for 5 min followed by 35 cycles of denaturation at 95° C. for 30 seconds, annealing Temp for 30 seconds and extension at 72° C. for 45 seconds. This was followed by final extension at 72° C. for 10 min.

Primer Used:

For I strand synthesis: OligodT primer

For II strand synthesis:

Forward: 5' CAGCATCCCTACTCCCACCAG3'

Reverse: 5' CACCTCGGCTTCCACCTCTTG 3'

Product size: 219 bp.

Result

TABLE 6

The gene expression level of eNOS normalized to β-Actin of G2, G3, G4 treated cells

| Test Sample | Regulation in Terms of Folds* eNOS |
|---|---|
| Control | 1.00 |
| Pregabalin (125 μg/ml) | 1.58 |
| G2 | 1.25 |
| G3 | 1.25 |
| G4 | 1.42 |

*Values shown in term of the fold.

DISCUSSION AND CONCLUSION

The test substance, G2, G3 and G4 were evaluated for its modulatory effect on eNOS gene expression in H9C2. The level of mRNA expression was analyzed by reverse transcriptase PCR. TNF-alpha was employed as positive control for the eNOS gene expression. Endothelial nitric oxide synthase gene (eNOS) expression was over expressed by the treatment with G2, G3 and G4 by 0.25, 0.25 and 0.42 folds at tested doses in H9C2 cells, respectively as compared to the control. Combination of test products G4 exhibited enhancement of eNOS expression by 0.42 folds over control, where the standard product Lyrica® up-regulated the eNOS gene expression by 0.58 fold over control.

Among the test products, G4 showed greater up-regulation of eNOS expression.

We claim:

1. A synergistic nutritional composition(s) for treating neuropathic pain comprising a therapeutic exogenous blend of palmitoylethanolamide (PEA) and standardized red spinach extract with enriched nitrate content, wherein the PEA and the standardized red spinach extract with enriched nitrate content are present in the ratio of 1:0.1 to 1:5; and PEA and nitrate of the standardized red spinach extract are present in the ratio of 1:0.01 to 1:0.5, along with pharmaceutically acceptable excipients.

2. The synergistic nutritional composition according to claim 1, wherein the PEA is present in the range of 40-80% and the standardized red spinach extract enriched with nitrate content is present in the range of 10-50% by weight of total composition.

3. The synergistic nutritional composition according to claim 1, wherein the nitrate of standardized red spinach extract is present in the range of 9.0 to 12.0% by weight of the standardized red spinach extract and 1.0 to 5.0% by weight of the total composition.

4. The synergistic nutritional composition according to claim 1, wherein the standardized red spinach extract enriched with nitrate content comprises inorganic nitrate and/or organic nitrate or combination thereof, preferably enriched nitrate content is inorganic nitrate.

5. The synergistic nutritional composition according to claim 1, wherein the pharmaceutically acceptable excipients are selected from a diluent, a binder, a lubricant, a glidant, an additive, a surfactant, a solvent or mixture thereof; wherein the diluent is present in the range of 1 to 40%; the binder is present in the range of 0.1 to 20%; the lubricant is present in the range of 0.1 to 5.0%; the glidant is present in the range of 0.1 to 5.0%; the additive is present in the range of 1 to 20%; and the surfactant is present in the range of 0.1 to 5.0%, by weight of total composition.

6. The synergistic nutritional composition according to claim 1, wherein oral administration of an effective dose the composition improves analgesic activity by more than 50% over control in a subject in need thereof.

7. The synergistic nutritional composition according to claim 1, wherein the oral administration of the effective dose of the composition improves vasodilatation by increasing eNOS expression by more than 0.40 fold over control in a subject in need thereof.

8. The synergistic nutritional composition according to claim 1, wherein the oral administration of the effective dose of the composition is used for treating diabetic peripheral neuropathy and/or small fiber neuropathy.

9. A method of treatment of neuropathic pain in a subject in need thereof, wherein the method comprising, oral administration of therapeutically effective amount of a nutritional composition comprising an exogenous synergistic blend of palmitoylethanolamide (PEA) and standardized red spinach extract enriched with nitrate content, wherein the PEA and the standardized red spinach extract enriched with nitrate content are present in the ratio of 1:0.2 to 1:2; and PEA and nitrate of standardized red spinach extract are present in the ratio of 1:0.02 to 1:0.2, along with pharmaceutically acceptable excipients.

10. The method of treatment according to claim 9, wherein the PEA is present in the range of 40.0% to 80.0% by weight of total composition.

11. The method of treatment according to claim 9, wherein the PEA is in micronized form with improved bioavailability and solubility.

12. The method of treatment according to claim 9, wherein the standardized red spinach extract enriched with nitrate content is present in the range of 10.0% to 50.0% by weight of total composition.

13. The method of treatment according to claim 9, wherein the nitrate of the standardized red spinach extract is present in the range of 9.0% to 12.0% by weight of the standardized red spinach extract and 1.0 to 5.0% by weight of total composition.

14. The method of treatment according to claim 9, wherein the red spinach extract is an aqueous extract of *Amaranthus cruentus* leaves.

15. The method of treatment according to claim 9, wherein the neuropathic pain is diabetic peripheral neuropathy, small fiber neuropathy, post-herpetic neuralgia, trigeminal neuralgia, phantom limb pain, carpal tunnel syndrome, sciatica, pudendal neuralgia, complex regional pain syndrome, sensory polyneuropathies, mono-neuropathies, or central pain syndrome, headaches, joint pain, backaches, sinus pain, muscle pain, nerve pain, and pain affecting specific parts of the body, such as shoulders, pelvis, and neck, and/or pain that is associated with lower back pain, lumbopelvic pain, arthritis, headache, multiple sclerosis, fibromyalgia, shingles, nerve damage, cancer, a demyelinating neuropathy, chemotherapy induced neuropathy, HIV neuropathy, post herpetic neuropathy or postoperative pain.

16. The method of treatment according to claim 15, wherein the neuropathic pain is diabetic peripheral neuropathy and/or small fiber neuropathy.

17. The method of treatment according to claim 9, wherein the composition exhibits improved analgesic potential over control, preferably more than 54.0% analgesic effect at 180 min over control.

18. The method of treatment according to claim 9, wherein the composition exhibits improved eNOS expression by 0.42 folds over control.

* * * * *